United States Patent [19]

Onufryk

[11] Patent Number: 4,673,263

[45] Date of Patent: Jun. 16, 1987

[54] OPTICAL IMAGE DEFLECTOR ASSEMBLY AND METHOD FOR LOCATING VISUALLY SENSITIVE PERIPHERAL AREAS OF AN EYE, AND DETERMINING CORRECTIVE PRISMATIC EYE GLASSES THEREFORE

[76] Inventor: Michael Onufryk, 9 Wickford Way, Fairport, N.Y. 14450

[21] Appl. No.: 435,767

[22] Filed: Oct. 21, 1982

[51] Int. Cl.[4] .......................... G02C 1/00; G02C 7/14
[52] U.S. Cl. ....................................... 351/158; 351/50
[58] Field of Search .......................... 351/50, 158, 227; 350/301

[56] References Cited

U.S. PATENT DOCUMENTS

| 951,755 | 3/1910 | Crane | 350/618 |
|---|---|---|---|
| 1,318,812 | 10/1919 | Smith | 350/618 X |
| 2,255,197 | 9/1941 | Thomas | 350/301 |
| 2,364,670 | 12/1944 | Stamy et al. | 350/301 |
| 2,594,698 | 4/1952 | Thomas | 351/175 X |
| 3,058,392 | 10/1962 | Primeau | 351/158 |
| 3,628,854 | 12/1971 | Janpolsky | 351/175 |

OTHER PUBLICATIONS

Jalie, "The Prismatic Effect at any Point on a Lens" The Optician, vol. 149, 6/18/65.

The Optician, "Cemented Prism for Severe Field Loss", vol. 163, Jul. 7, 1972.
Krimsky, Amer. Acad. of Opthal & Otolaryn., Oct. 1949.
*Distortion of Image by Prism*-by Kenneth N. Ogle, Journal of the Optical Society of America, vol. 41, No. 12 (Dec., 1951).
*Distortion of Opthalmic Prisms*-by Meredith W. Morgan, America Academy of Optometry and Archives of America Academy of Optometry, Jun., 1963.
*Visual Performance and Optical Properties of Fresnell Membrane Prisms*-by Anthony J. Adams et al. American Journal of Optometry and Archives of American Academy of Optometry, vol. 48, No. 4 (Apr., 1971).

*Primary Examiner*—Rodney B. Bovernick
*Attorney, Agent, or Firm*—Cumpston & Shaw

[57] ABSTRACT

A pair of rotatable optical image deflector assemblies are disclosed which are detachably mounted via an adapter bracket to a conventional eye testing apparatus. Each optical image deflector assembly has a fixed light reflecting optical element, and a pivotal reflecting optical element. The optical image deflector assembly directs light onto a peripheral area of an eye, and scans an arcuate portion of the area upon pivotal movement of the pivotal optical element.

11 Claims, 9 Drawing Figures

OPTICAL IMAGE DEFLECTOR ASSEMBLY AND METHOD FOR LOCATING VISUALLY SENSITIVE PERIPHERAL AREAS OF AN EYE, AND DETERMINING CORRECTIVE PRISMATIC EYE GLASSES THEREFORE

BACKGROUND OF THE INVENTION

1. Field of the Invention

The present invention relates to visual examining and sight corrective apparatus, and more particularly to an optical image deflector assembly and method for use in scanning eyes, locating visually sensitive peripheral areas thereof, and determining corrective prismatic eye glasses adapted to focus light on the visually sensitive peripheral areas of the eyes.

2. Description of the Prior Art

U.S. Pat. No. Re. 28,921 discloses an automatic visual sensitivity and blind spot measuring apparatus comprising a device for projecting a spot at different locations on a screen to be viewed by the person being tested along with means for the person to indicate perception of the spot for subsequent evaluation. The device further comprises means for projecting the spot in different positions in the field of vision of the person being tested.

U.S. Pat. No. 1,990,107 relates to a reflectoscope used in the examination of an eye. The reflectoscope comprises mirrors for reflecting an eye focused image around an operator so that the eye can be observed in the correct orientation to prescribe lenses for correcting refractive disfunctions. The image is reflected onto the normally sensitive portion of the eye.

U.S. Pat. No. 4,264,152 relates to apparatus for moving an image of a target in certain preselected ways to stimulate certain types of eye movements in the subject.

U.S. Pat. No. 4,298,253 relates to apparatus for presenting test images to a viewer at different distances without modifying the visual angle or acuity of the images.

U.S. Pat. No. 3,423,151 relates to auxiliary prismatic lenses mountable on an eye glass frame for use by persons having cataracts. The lenses extend the field of view of the person beyond that provided by ordinary lenses by focusing images beyond the range of the normal lenses onto the pupil of the eye.

U.S. Pat. No. 2,442,849 relates to a method for producing a pair of lenses for providing balanced binocular vision to a greater degree than was previously possible. The invention particularly relates to the correction of conventional disorders such as refractive disorders.

In addition to the prior art patent literature, an eye disease is known called neovascular senile macular degeneration (N.S.M.D.) in which central vision is greatly impaired, often resulting in blindness by virtue of blood vessels growing into the macula of the eye. The macula controls central vision in the retina, and the rest of the retina is used for peripheral vision. The problem of central vision impairment and blindness due to N.S.M.D. and other problems such as tunnel vision are substantially overcome by the optical image deflector assembly of this invention.

SUMMARY OF THE INVENTION

In accordance with a preferred embodiment of the invention, a pair of rotatable optical image deflecting assemblies and method are disclosed in which the assemblies are preferably detachably mounted via an adapter onto a standard eye testing apparatus. The mechanical center of each optical assembly is aligned with the optical center of an eye. The optical assemblies are useful in locating the most visually sensitive peripheral portions of the retina, and determining the prism diopters required for corrective prismatic eye glasses for focusing images thereon.

Each optical image deflecting assembly has a fixed light reflecting optical element such as a mirror and a pivotal reflecting optical element such as a mirror. Light received from one of the mirrors is reflected onto a peripheral area of an eye for scanning an arcuate portion of the area upon pivotal movement of the pivotal mirror. Means are provided for selectively incrementally rotating each optical assembly through a complete revolution. The pivotal optical element is pivoted at each incremental position for scanning an annular peripheral area of each eye and locating the most visually sensitive areas therein. After determining the prism diopters required and testing with trial lens(es), a prismatic lens(es) is then determined for each examined eye and mounted in an eye glass frame to provide the best possible eye sight for the eyes.

In a more specific aspect of the invention, each optical assembly comprises a first ring secured to the frame, and a second ring rotatably mounted on the first ring. The fixed and pivoting optical elements are mounted on diametrically opposed portions of the second ring.

The invention and its advantages will become more apparent from the detailed description of the invention presented below.

DETAILED DESCRIPTION OF THE INVENTION

Figure 1:
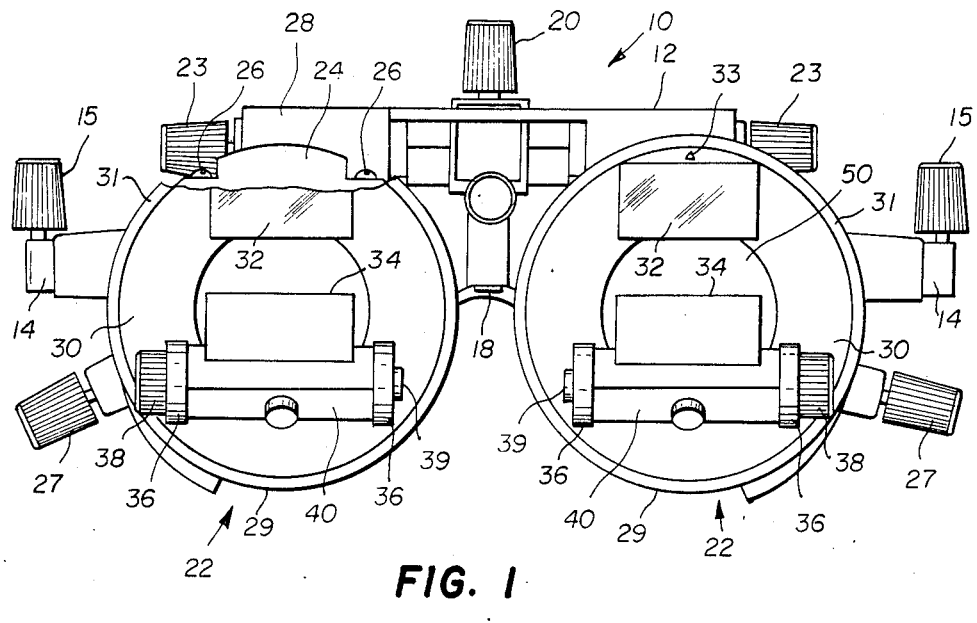
FIG. 1 is a front elevational view of a preferred embodiment of an eye examining apparatus of this invention with a portion thereof broken away to show a portion of the mounting bracket.
Figure 2:
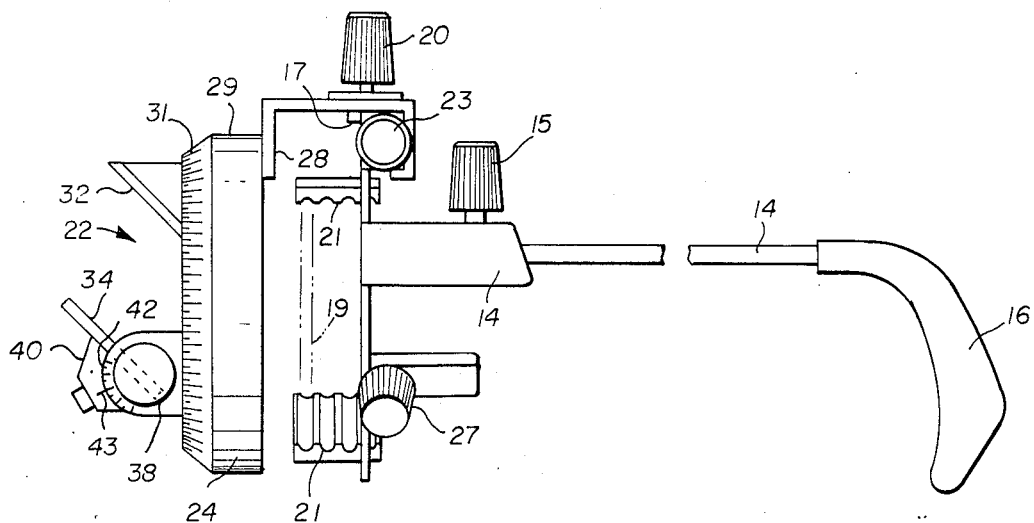
FIG. 2 is a side elevational view of the eye examining apparatus of FIG. 1.
Figure 3:
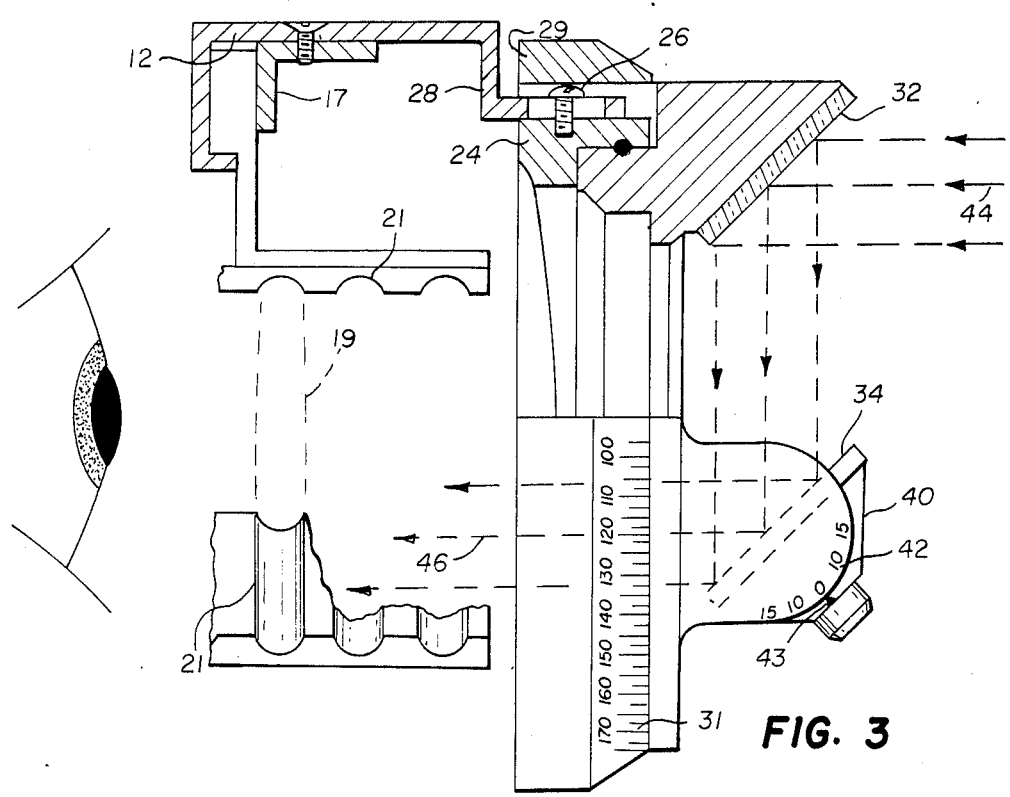
FIG. 3 is an enlarged side elevational view, partially in section, of an optical image deflecting assembly mountable by a bracket to a standard trial lens holder.

With reference to FIGS. 1-3, an eye examining apparatus 10 is disclosed comprising an adapter bracket 12 having temple bars 14 hingedly connected at one of the ends thereof to end portions of the bracket. The opposite ends of temple bars 14 have suitable ear pieces 16 for mounting bracket 12 onto the head of a person whose eyes are to be examined. The temple bars 14 may have conventional adjusting means, not shown, by which the length of the bars may be changed to adjust the position of the bracket relative to the person's eyes. A nose piece 18 is mounted on bracket 12 and has conventional adjusting means 20 for raising or lowering bracket 12 relative to the person's eyes. A conventional trial lens holding means 21 is affixed to bracket 12 by an L-shaped retainer 17 (FIG. 3) and extends downwardly from frame 12 for holding trial lens(es) 19. The trial lens holding means 21 is laterally, tiltably and rotatably adjustable by any suitable adjusting means 23, 25 and 27 respectively.

A pair of identical optical image deflector assemblies 22 are detachably mounted on bracket 12 in laterally spaced relation. Each optical image deflector assembly 22 comprises a first annular ring 24 secured by screws 26 to slotted, spaced lugs 28 extending from bracket 12, as best seen in FIGS. 1 and 3. Alternatively, each optical assembly 22 can be releasably connected to bracket 12 by any suitable quick-disconnect means, not shown. The first ring 24 has a cylindrical inner surface for rotatably receiving an outer cylindrical surface of a second annular ring 30. An "0" ring is positioned in facing grooves in the inner and outer surfaces for releasably securing the first and second rings 24, 30 together for relative rotatable movement therebetween by manual means, or any suitable pinion and ring gear, not shown. An annular scale member 29 is secured to ring 24, and is provided with indicia 31 that cooperates with an index 33 on ring 30 to indicate the angular position of ring 30 during rotation thereof.

An optical element extends laterally from one side of ring 30 and has a surface inclined 45° to the axis of ring 30 for supporting a fixed reflecting mirror 32 affixed thereto. An optical element comprising a reflecting mirror 34 is pivotally mounted on ring 30 in a position diametrically opposed from fixed mirror 32. A pair of spaced, laterally extending side walls 36 have screws 38, 39 extending through openings in the walls into threaded bores at one end of support member 40. Pivoting mirror 34 is secured to support member 40, and screws 38, 39 form a pivot for the support member and mirror. Support member 40 has an index 43 which cooperates with a scale 42 on a wall 36 for indicating the pivotal position of the pivoting mirror 34 relative to a zero degree position in which the pivoting mirror is parallel to fixed mirror 32. By tightening one or both of the screws 38, 39, the pivoting mirror 34 can be locked in any pivotally selected position.

Figure 4:
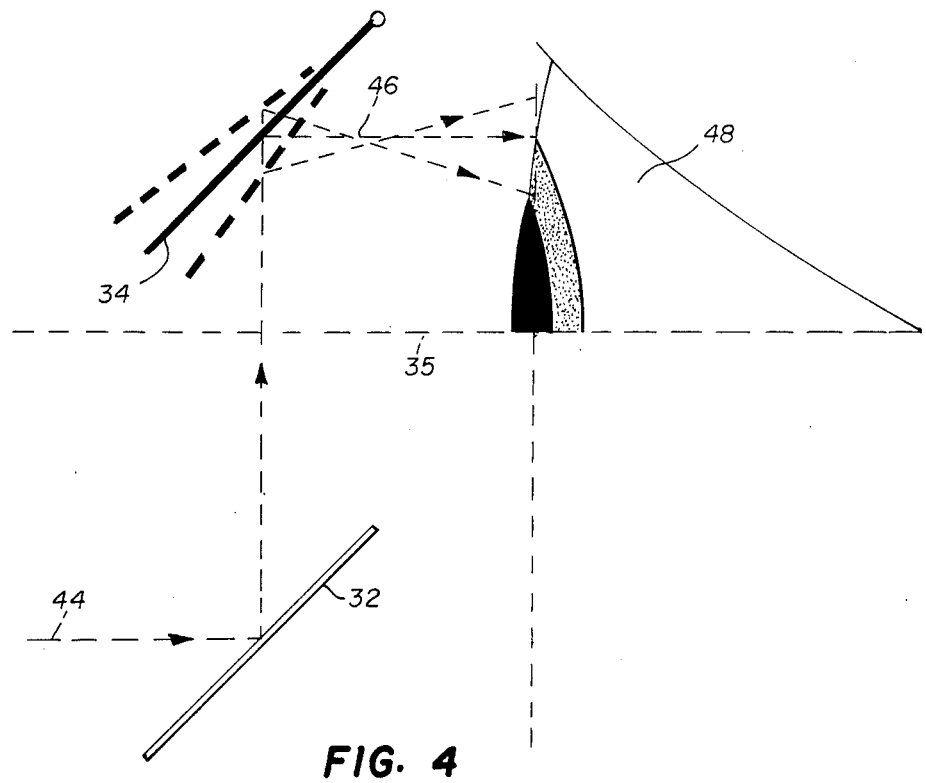
FIG. 4 is a schematic view of the optical system of the eye examining apparatus.

With reference to FIG. 4, a schematic view of an optical assembly 22 for locating the most sensitive peripheral area of an eye 48 is rotatable about its axis 35, which is coincident with the optical axis 0 of the eye. A normal incident light ray 44 strikes fixed reflecting mirror 32, and is reflected onto a parallel pivotal reflecting mirror 34, which reflects a normal light ray 46 onto a peripheral area of eye 48. By pivoting reflecting mirror 34, the reflected light ray scans an arcuate peripheral area of the eye, and the total angle through which the mirror is pivoted in scanning the sensitive area is referred to as the wedge angle A.

Figure 5:
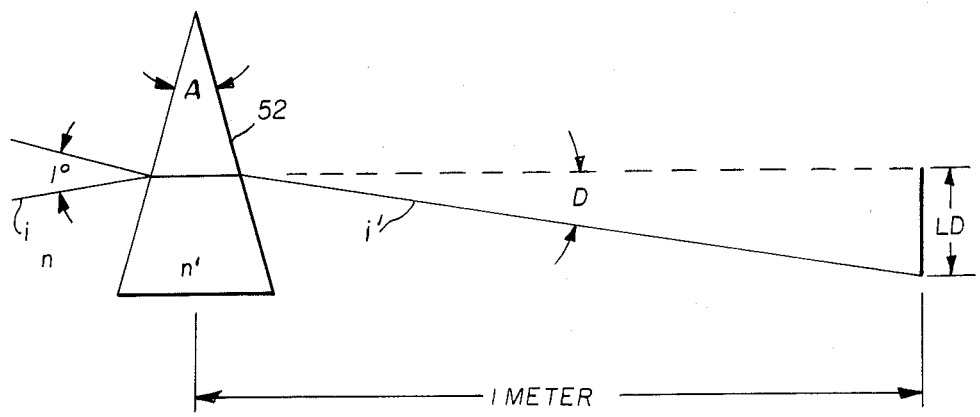
FIG. 5 is a schematic view of a prism for deviating light rays in which all of the angles have been exaggerated for use in explaining conversion of a wedge angle to prism diopters.

To convert this wedge angle A to prism diopters or units of refractive power needed to laterally deviate light ray 46 from incident light ray 44, reference is made to FIG. 5. Prism diopters is defined as a linear deviation in centimeters which the prism produces at a distance of one meter when a ray passes through the prism at minimum deviation. For this conversion, a prism 52 of clear plastic having an index of refraction N' of 1.5 is used as compared to an index of refraction n for air of 1. Some assumptions are made such as the selection of a wedge angle A of 2°, for example, and disregarding the sines of small wedge angles when using Snell's law $n \sin \theta = n' \sin \theta'$ in which n, n' represent the indexes of refraction of the mediums and $\theta$, $\theta'$ the angles of incidence and refraction, respectively. Incident and refracted light rays designated i, i' respectively of 1° are used, although shown exaggerated in FIG. 5 for purposes of clarity. Accordingly, the deviation angle D in FIG. 5 is derived as follows:

$$D = (n' - n)A$$

$$D = (1.5 - 1)2$$

$$D = 0.5 \times 1$$

$$D = 1°$$

Then the linear deviation (LD) is computed as follows:

$$LD = (\tan 1°)(1 \text{ meter})$$

$$LD = 0.0175 \times 100 \text{ centimeters (CM)}$$

$$LD32 \ 1.75 \text{ cm}$$

Therefore, a factor for linear deviation in centimeters per degree of angle incidence is computed as follows:

$$\text{Factor} = 1.75/1 = 1.75$$

Now let us assume that in the aforementioned example illustrated with reference to FIG. 4, the wedge angle A for best peripheral vision was determined to be 9°. The incident angle which is one-half the wedge angle is read directly from scale 42 as 45°. Accordingly, to convert the wedge angle A to prism diopters, the distance the light must be deviated or refracted from the optical center of the eye for best peripheral vision is equal to the incident angle of 4.5° times the factor of 1.75, or 7.87 cm. Since a prism of one diopter bends light such that a refracted ray deviates one cm from the projected incident ray at a distance of one meter from the prism, the number of prism diopters needed is 7.87/1 or 7.87. In actual use, a prism 52 of eight prism diopters would be selected.

In the operation of the eye examining apparatus of this invention for determining a wedge angle A and prism diopters for best peripheral vision, the pivoting mirrors 34 and optical assemblies 22 are initially placed in their zero degree positions. In this position, the mirrors 32, 34 are aligned with vertical lines passing through the centers of the assemblies 22. An opaque lens 50 is placed in the lens holding means 21 for the eye that is not being tested. No lens of any type is placed in the trial lens holding means 21 for the eye to be tested at this time.

The eye examining apparatus 10 is placed on a person whose eyes 48 are to be tested, and the temple bars 14, nose piece 18 and lens holding means 21 are adjusted so that the mechanical centers of the mirror assemblies 22 are aligned with the optical centers of the eyes.

The mirror assembly 22 for the eye being tested is intermittently rotated through a complete revolution, stopping, for example, at each 10° (degree) position. It may be preferable to rotate the mirror assembly 180° in one direction, a return to the zero position, and then rotate 180° in the opposite direction. At each position, pivoting mirror 34 is pivoted plus or minus 15° to scan the arcuate peripheral area of the eye. At each position, the comments of the person being tested with regard to visual perception of bright areas or objects is noted. If visual perception is noted, the wedge angle that was required to note this perception is recorded along with the incident angle read directly from scale 42. The rotating procedure is repeated several times, each time advancing the starting position a few degrees until the entire annular peripheral area of the eye is tested. The recorded peripheral area of best vision and recorded incident and wedge angle A for that position is determined.

A Sloan-Lighthouse eye chart is placed or held approximately 40 cm from the person being tested. The rotating mirror assembly 22 for the eye being tested is rotated to the above-determined best angular position of peripheral vision. The pivoting mirror 34 is set at the center position of the determined wedge angle A, which is the recorded incident angle at that position. A plus 3 diopter trial lens is placed in the trial lens holding means 21. At this point, the determined wedge angle A can be converted to prism diopters as discussed earlier, and the calculated prism 52 and trial lens 54 may be used in the trial lens holding means 21 to measure the vision potential of the tested eye. Use of the mirrors 32, 34 are preferred, however, since they have practically no distortion and will provide a more accurate correction for the best peripheral vision.

A standard optical procedure is applied at this time, adding or subtracting diopters to the trial lens 54 and/or cylinders until the eye discerns objects at close range. If the person being tested cannot read the letters or numbers on the chart at the 40 cm distance, the chart is moved closer until the person can read a line on the chart. The resolution of the eye can be determined by measuring the chart distance from the eye and the size of the letters being read. For far distance viewing, the above procedure is repeated except that a Sloan letter low vision chart is used at distances of 0.75 meter, 1.5 meters and at 3 meters.

The aforementioned testing procedure is repeated for the other eye. After both eyes have been tested, the determined wedge angle A for each eye is converted to prism diopters by multiplying the recorded incident angle (one-half of wedge angle A) times 1.75 as indicated earlier. The optical assemblies 22 are removed from frame 12, and the calculated prisms 52 are placed in the lens holding means 21, and the trial lens holding means rotated until the apex of each prism is positioned at the angle of best peripheral vision for each eye 48. The trial lens(es) 54 for the best close vision of each eye is placed in the trial lens holding means 21 between the eye 48 and prism 52. At this time, the Sloan-Lighthouse chart is positioned or held at a distance 40 cm from the person being tested. The person is asked to read the charts to determine that there is no distortion or diplopia present, and to determine the best resolution for the eyes. This procedure is also repeated for the far distance viewing except the chart and trial lens(es) that were determined earlier for far distance viewing will be used.

Figures 6, 7, 7A:
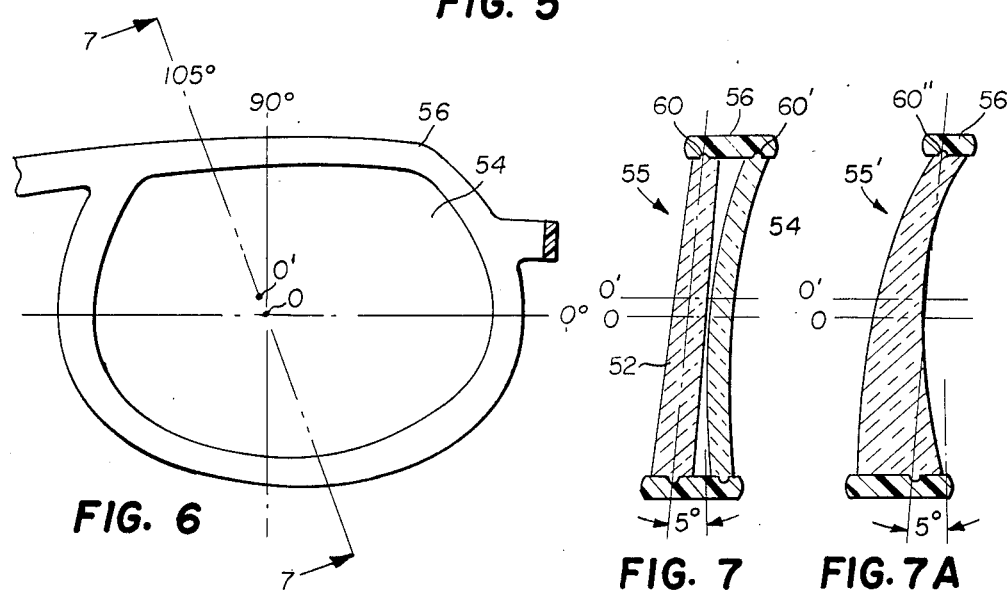
FIG. 6 is a segmental front elevational view of a prismatic lens eye glass.
FIG. 7 is a section view taken substantially along line 7—7 of FIG. 6.
FIG. 7A is a section view of a singular prismatic lens.

The combination of prism 52 and trial lens(es) 54 determined by the aforementioned testing procedure comprises a prismatic lens 55, 55' as seen in FIGS. 7, 7A respectively, and are mountable in the aforementioned determined orientation in the frame of eye glasses 56, seen in part in FIG. 6. Alternatively, the prism 52 can be mounted in a double frame, not shown, by means, such as clips or hinges, the corrective lens being mounted in one set of the frames, and the prism in the other set of frames. This type of frame(s) or mounting provide the means to design any combination of glasses, such as (1) a near and far distance combination, (2) reading glasses combined with either a near or far distance combination, (3) ultra-violet filter with either a near or far distance combination, etc.

A person having only peripheral vision cannot use bi-focals. Accordingly, two pair of eye glasses must be designed—one for long distance and one for short range.

When a person first wears eye glasses 56 with prismatic lenses 55, 55' he may see double and/or distorted images. The double images can be corrected by rotating the prisms 52 until the apex of both prisms are located precisely at the tested angular position of best peripheral vision. To reduce some prism distortion, a prism 52 having the next smaller prism diopter should be used. The phenomenon of wearing prismatic glasses for the first time is akin to a person wearing bi-focals or tri-focals for the first time.

For a person having full vision, the optical center of each corrective lens(es) 55, 55' is positioned from its zero axis to approximately 3 millimeters below the eye's optical axis 0 so that the person may walk with his head in a normal attitude while looking forward.

For a person having peripheral vision only, a re-positioning of the optical axis (0) of approximately 5 millimeters towards the position of best peripheral vision should be made to insure that images entering the eye will be perpendicular to the peripheral area. The new position of the optical axis designated 0' is illustrated in exaggerated form in FIG. 6 extending at 105° which, in this example, was selected as the position of best peripheral vision. Also, to help eyes with peripheral vision to focus on frontal objects, the prismatic lens 55 is tilted approximately 5 degrees towards the center of the best peripheral vision. This is achieved in FIGS. 7, 7A by grinding lens retainer rings 60, 60', 60" respectively which are offset from the vertical by 5°. Accordingly, when the prismatic lenses 55, 55' are mounted in eye glass frames 56, the prismatic lenses will be tilted 5° toward the center of the best peripheral vision.

The displacement of the optical axis 0 and the tilt of the prismatic lenses 55, 55' will increase the refractive power (prism diopters) of the prismatic lens system without increasing the size of the prism or correction lens(es). This reduces distortion, prism thickness, and the combined weight of the eye glasses 56 to a minimum. The increase in prism diopters depends on prism diopter size and power of the corrective lens. In one example, a prismatic lens system had a corrected lens of plus 4.5 diopters combined with a prism of 8 prism diopters. Due to displacement of the optical axis 0 and tilting of the prismatic lenses 55, 55', the refractive power of the system was increased approximately 3 prism diopters. The prismatic lens then responded as a 11 prism diopter lens. The aforementioned displacement and tilting of the lenses will also facilitate walking with one's head in a normal attitude while looking in the forward direction.

Figure 8:
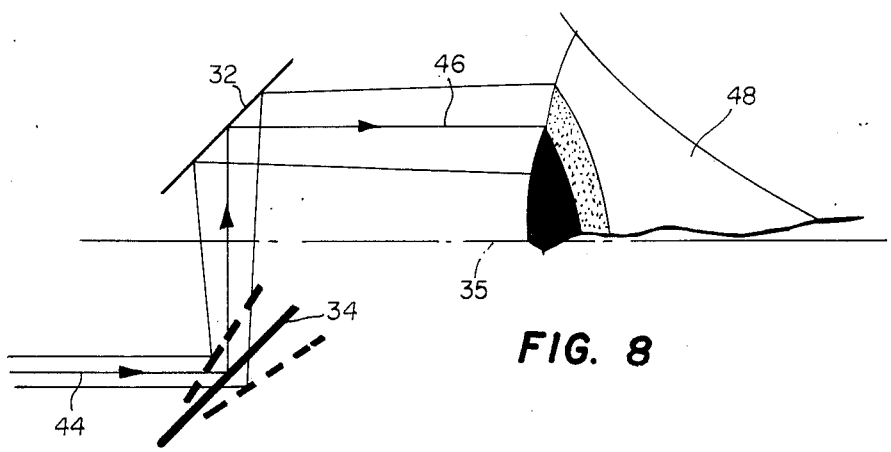
FIG. 8 is a schematic view similar to FIG. 4 of an optical system for use in examining persons having tunnel vision.

With reference to FIG. 8, a modification of this invention is illustrated for use in examining the eye of a person having tunnel vision, for example. In this embodiment of the invention, the positions of the fixed and pivotal mirrors 32, 34 respectively are reversed. The eye examining apparatus is used in the same manner as described heretofore except that the rotatable ring 30 is locked on the zero axis of the eye and the pivoting mirror 34 is then pivoted to determine the prism diopters required for best lateral vision for each eye. The eye glasses are then designed with determined prism diopters and corrective lens(es) 54 to provide lateral images to the visually sensitive central area of each eye to enlarge its field of vision.

While a presently preferred embodiment of the invention has been shown and described with particularity, it will be appreciated that various changes and modifications may suggest themselves to one having ordinary skill in the art upon being apprised of the present invention. It is intended to encompass all such changes and modifications as fall within the scope and spirit of the appended claims.

I claim:

1. An eye examining apparatus for scanning an eye and locating visually sensitive peripheral areas of the eye comprising:
   a frame;
   a rotatable optical assembly mounted on said frame with the mechanical center of said optical assembly aligned with the optical center of an eye to be scanned;
   said optical assembly having a fixed light reflecting optical element and a pivotal light reflecting optical element, said fixed and pivotal optical elements cooperating together for directing light onto a peripheral area of an eye and scanning an arcuate portion of said area upon pivotal movement of said pivotal optical element; and
   means for selectively incrementally rotating said optical assembly a revolution and pivoting said optical element at each incremental movement for scanning an annular peripheral area of an eye and locating any visually sensitive areas wherein.

2. The eye examining apparatus according to claim 1 wherein said optical assembly comprises a first ring secured to said frame, and a second ring rotatably mounted on said first ring, and said fixed and pivoting optical elements comprise mirrors mounted on said second ring.

3. The eye examining apparatus according to claim 1, and further comprising adjustable nose piece means on said frame for adjusting the center of said optical assembly in alignment with the optical center of the eye to be scanned.

4. The eye examining apparatus according to claim 1, and further comprising a correction lens holding means mounted on said frame in alignment with said optical assembly.

5. The eye examining apparatus according to claim 1 wherein said optical assembly comprises a first ring secured to said frame, and a second ring rotatably mounted on said first ring, and said fixed and pivoting optical elements comprise mirrors mounted on diametrically opposed portions of said second ring, said apparatus further comprising temple bars on said frame for releasably securing said frame onto a person in an eye scanning position, adjustable nose piece means on said frame for adjusting the center of said optical asembly in alignment with the optical center of an eye to be scanned, and trial lens holding means mounted on said frame in alignment with said optical assembly.

6. A rotatable optical assembly for use in scanning an eye and locating visually sensitive peripheral areas of the eye comprising:
   a support member;
   a member rotatably mounted on said support member;
   a fixed light reflecting optical element mounted on said rotatable member;
   a pivotal light reflecting optical element mounted on said rotatable member and cooperating with said fixed optical element for use in directing light onto a peripheral area of an eye, scanning an arcuate portion of said area upon pivotal movement of said pivotal optical element, and locating any visually sensitive areas in said peripheral area.

7. The rotatable optical assembly according to claim 6 wherein said support member comprises a first ring, said rotatable member comprises a second ring rotatably mounted on said first ring, and said fixed and pivoting optical elements comprise mirrors mounted on said second ring.

8. The rotatable optical assembly according to claim 7 wherein said mirrors are mounted on diametrically opposed portions of said second ring.

9. The rotatable optical assembly according to claim 6 wherein said support member comprises a first ring, said rotatable member comprises a second ring rotatably mounted on said first ring, said fixed and pivoting optical elements comprise mirrors mounted on diametrically opposed portions of said second ring, said assembly further comprising first indicia on said first ring, a first index on said second ring cooperating with said first indicia to indicate the angular position of said second ring relative to said first ring, a second indicia on said second rign, and a second index on said pivoting mirror cooperating with said second indicia to indicate the angular position of said pivoting mirror relative to said second ring.

10. A method of scanning an eye and locating visually sensitive peripheral areas of the eye comprising the steps of:
   directing light by means of an optical assembly comprising a pivotal optical element onto a peripheral area of an eye;
   rotating the optical assembly about the optical axis of the eye in incremental steps; and
   pivoting the pivotal optical element through a preselected angle at each incremental step for scanning an annular peripheral area of each eye and locating any visually sensitive areas therein.

11. A method according to claim 10 wherein the optical assembly comprises an annular rotatable ring having a fixed optical element mounted thereon, and the pivotal optical element comprises a mirror mounted on the ring diametrically opposed from the fixed optical element.

* * * * *